United States Patent
Rana et al.

(10) Patent No.: US 9,757,352 B2
(45) Date of Patent: *Sep. 12, 2017

(54) PARENTERAL DOSAGE FORM OF AMIODARONE

(71) Applicant: SUN PHARMACEUTICAL INDUSTRIES LIMITED, Mumbai (IN)

(72) Inventors: Amar Kishorbhai Rana, Baroda (IN); Shantaram Pawar, Baroda (IN); Prashant Kane, Baroda (IN); Subhas Balaram Bhowmick, Baroda (IN); Maheshkumar Parasmal Soni, Baroda (IN); Milan Mohanbhai Vasoya, Baroda (IN); Samarth Kumar, Baroda (IN)

(73) Assignee: SUN PHARMACEUTICAL INDUSTRIES LIMITED, Mubai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/490,314

(22) Filed: Apr. 18, 2017

(65) Prior Publication Data

US 2017/0216243 A1 Aug. 3, 2017

Related U.S. Application Data

(63) Continuation of application No. 14/859,733, filed on Sep. 21, 2015, now Pat. No. 9,642,828.

(30) Foreign Application Priority Data

Sep. 23, 2014 (IN) .................... 3030/MUM/2014

(51) Int. Cl.
*A61K 9/00* (2006.01)
*A61K 31/343* (2006.01)

(52) U.S. Cl.
CPC .......... *A61K 31/343* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 5,234,949 A | 8/1993 | Ehrenpreis et al. | |
| 6,479,541 B1 | 11/2002 | Kipp | |
| 7,067,143 B2 | 6/2006 | Doty | |
| 2012/0142768 A1 | 6/2012 | Mosher | |

OTHER PUBLICATIONS

Viaflex [(on-line website: http://www.baxtermedicationdeliveryproducts.com/drug-delivery/viaflex.html (last access date: Jul. 31, 2016).
Campbell, Suzanne, et al., "Stability of amiodarone hydrochloride in admixtures with other injectable drugs," XP-001107000; vol. 53, Apr. 1986; American Journal of Hospital Pharmacy; pp. 917-921.
Wayback machine [on-line] website: https://web.archive.org/web/20160430131618/hppt://baxtermedicaliondeliveryproducts.com/drug-delivery/viatlex.html.last access date: 2016-07-310].

*Primary Examiner* — Ernst V Arnold
*Assistant Examiner* — Kyung Sook Chang
(74) *Attorney, Agent, or Firm* — Sughrue Mion, PLLC

(57) ABSTRACT

The present invention relates to a stable, sterile, ready to administer parenteral dosage form of amiodarone or its pharmaceutically acceptable salt. Particularly, the present invention provides a stable, sterile, ready to administer parenteral dosage form of amiodarone comprising an aqueous solution comprising amiodarone or its pharmaceutically acceptable salt, an acid, and a polyol, wherein the pH of the solution is in the range of about 2.0 to 4.0, wherein the solution is filled in a plastic container and wherein the solution is free of a solubilizer.

8 Claims, No Drawings

PARENTERAL DOSAGE FORM OF AMIODARONE

This application is a Continuation Application of U.S. application Ser. No. 14/859,733, filed Sep. 21, 2015, and claims benefit to Indian Application No. 3030/MUM/2014, filed Sep. 23, 2014.

FIELD OF THE INVENTION

The present invention relates to a stable, sterile, ready to administer parenteral dosage form of amiodarone or its pharmaceutically acceptable salt.

BACKGROUND OF THE INVENTION

Amiodarone hydrochloride is (2-butyl-3-benzo-furanyl) [4-[2-(diethylamino)ethoxy]-3,5-diiodophenyl]methanone hydrochloride and have the following structural formula

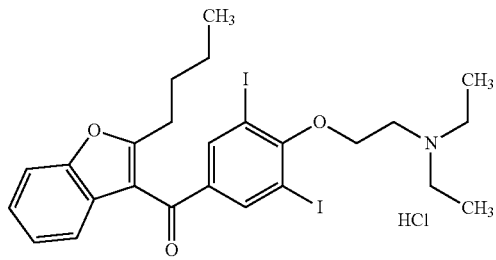 [SMILES: CCCCc1oc2ccccc2c1C(=O)c1cc(I)c(OCCN(CC)CC)c(I)c1 ; Cl]

Amiodarone is a class III antiarrhythmic drug. Approved products include tablets (oral) as well as injectable injections. Two injectable dosage forms approved in the United States include—CORDARONE® and NEXTERONE®. These are indicated for initiation of treatment and prophylaxis of frequently recurring ventricular fibrillation (VF) and hemodynamically unstable ventricular tachycardia (VT) in patients refractory to other therapy.

CORDARONE® is an injection solution concentrate of Amiodarone, having 50 mg/ml Amiodarone hydrochloride. Each mL of the amiodarone I.V. formulation contains 50 mg of amiodarone hydrochloride, 20.2 mg of benzyl alcohol, 100 mg of polysorbate 80, and water for injection.

NEXTERONE® Premixed Injection is available as a diluted, nonpyrogenic, iso-osmotic solution for intravenous administration, each mL containing 1.5 mg of amiodarone HCl, USP; 15 mg of betadex sulfobutyl ether Sodium (a cyclodextrin), 0.362 mg of citric acid anhydrous, 0.183 mg of sodium citrate dihydrate and 42.1 mg dextrose anhydrous in water for injection.

Surprisingly, the inventors of the present invention found out a ready-to-administer parenteral dosage form of amiodarone, which does not make use of any solubilizers such as surfactant, for example polysorbate 80 and complexing agents like cyclodextrins, but yet provides a stable, clear aqueous solution of amiodarone. Further, this aqueous solution, more importantly, when stored in plastic containers do not show any signs of sorption to the containers.

SUMMARY OF THE INVENTION

The present invention provides a stable, sterile, ready to administer parenteral dosage form of amiodarone comprising an aqueous solution comprising:

a. amiodarone or its pharmaceutically acceptable salt,
b. an acid, and
c. a polyol,
wherein the pH of the solution is in the range of about 2.0 to 4.0,
wherein the solution is filled in a plastic container,
wherein the solution is free of a solubilizer.

DESCRIPTION OF THE INVENTION

The term "sterile" or 'sterilized' as used in the context of the invention, means a solution that has been brought to a state of sterility and the solution complies with the sterility requirements of the standard Pharmacopoeias like United States Pharmacopoeias (USP).

The term "stable" as used herein means that the dosage form of the present invention comprising the aqueous solution of amiodarone is physically as well as chemically stable as demonstrated by compliance to acceptable specification when the dosage form is stored at room temperature (about 25° C.) and at 2-8° C. for twelve months, preferably eighteen months, more preferably 24 months or longer. Preferably, the term "stable" signifies that when the dosage form of the present invention comprising the aqueous solution of amiodarone is stored at room temperature (about 20-30° C.) the total impurities remained below 2.5% and the solution showed no signs of precipitation. The total impurities include both known impurities and unknown impurities. The known impurities that are detected and quantified include—Impurity A {(2-butylbenzofuran-3-yl)[4-[2-(diethylamino) ethoxy]phenyl] methanone}; Impurity B {(2-butylbenzofuran-3-yl)[4-[2-(ethylamino)ethoxy]-3,5-diiodophenyl] methanone}; Impurity C {(2-butylbenzofuran-3-yl)[4-[2-diethylamino)ethoxy]-3-iodophenyl] methanone}; Impurity D {(2-butylbenzofuran-3-yl)(4-hydroxy-3,5-diiodophenyl) methanone}; Impurity E {(2-butylbenzofuran-3-yl)[4-hydroxyphenyl) methanone}; Impurity F {(2-butylbenzofuran-3-yl)(4-hydroxy-3-iodophenyl) methanone}; Impurity G [4-[2-(diethylamino)ethoxy]-3,5-diiodophenyl][2-[(1RS)-1-methoxybutyl]benzofuran-3-1]methanone}; Impurity H {(2-chloroethyl) diethylamine}; and the impurities 2-Buthyl-3-Benzofuranyl 4-Methoxyphenyl ketone and 2-Butyl Benzofurane.

Suitably, the aqueous solution of amiodarone or its pharmaceutically acceptable salt remains chemically stable wherein various parameters such as the drug content (assay of amiodarone) and content of related substances, i.e. known and unknown impurities remains within specified limits such as those specified according to ICH guidelines, upon storage at room temperature (about 25° C.) and at refrigerated conditions (2-8° C.), for prolonged period of time such as for at least 12 months, preferably for 18 months, more preferably 24 months or longer. Suitably, the value of assay of amiodarone remains within the specified limit of 90-110% by weight of the label claim; and the total impurities remain below 2.5%. Suitably, the solution also remains physically stable, with no precipitation or crystallization or color change upon storage and the value of percentage transmittance of the solution remaining greater than 90%, preferably greater than 95%.

The term "ready-to-administer" as used herein means that the drug solution is suitable for direct intravenous administration or infusion or injection and no intermediate steps of dilution or reconstitution are required before parenteral administration of the drug solution to the patient. The aqueous drug solution can be directly administered parenterally from the container of the dosage form. The term "ready-to-administer" is synonymous with "ready-to-infuse" or ready-to-inject". The aqueous solution of the present invention is suitable for direct intravenous administration, that is, it is "ready-to-infuse". The intravenous administration does not require any steps or handling or manipulation before administration and can be directly administered/infused to the patient. The ready-to-administer parenteral dosage form according to the present invention avoids the inconvenience of reconstituting or diluting a lyophilized or concentrated parenteral formulation into infusion diluents prior to infusion, as well as eliminates the risk of any potential calculation or dilution error as well as risk of microbiological contamination during handling.

The ready-to-administer parenteral dosage form of the present invention comprises an aqueous solution comprising therapeutically effective amount of amiodarone or its pharmaceutically acceptable salt, an acid and a polyol, wherein the solution is filled in a plastic container and wherein the solution is free of solubilizers.

In one embodiment, the present invention provides a ready-to-administer parenteral dosage form comprising an aqueous solution comprising therapeutically effective amount of amiodarone or its pharmaceutically acceptable salt, an acid and a polyol, wherein the pH of the solution is in the range of about 2.0 to 4.0, wherein the solution is filled in a plastic container and wherein the solution is free of solubilizers.

Alternatively, the present invention provides a ready-to-administer parenteral dosage form comprising an aqueous solution consisting essentially of therapeutically effective amount of amiodarone or its pharmaceutically acceptable salt, an acid and a polyol, and wherein the solution is filled in a plastic container. By the phrase 'consisting essentially of' as used herein means that the aqueous solution of amiodarone or its pharmaceutically acceptable salt contains an acid and polyols, and not any solubilizers such as complexing or chelating agents like cyclodextrins or surfactants such as for example polysorbate 80, tween 80 etc. These solubilizers do not include excipients such as cosolvents for example, glycols and the like.

In one embodiment, the ready-to-administer parenteral dosage form of the present invention is free of solubilizers such as complexing or chelating agents like cyclodextrins or surfactants such as for example polysorbate 80, tween 80 etc. Use of surfactants and/or complexing or chelating agents like cyclodextrins in directly administered intravenous parenteral dosage forms are generally not desirable as they may cause toxic or adverse reactions such as hypersensitivity reactions. Also, the parenteral aqueous solutions having surfactants if not handled properly may result in frothing of the solution, which is undesirable and makes the solution unsuitable for infusion. Since amiodarone have very low intrinsic water solubility, it is difficult to formulate a water-based parenteral formulation of amiodarone and further it is difficult to get a solution that is stable. Prior arts report use of such surfactants and complexing agents to prepare aqueous solution of amiodarone.

Surprisingly, the inventors of the present invention have developed a ready-to-administer parenteral dosage form of amiodarone, which does not make use of solubilizers like surfactants and complexing agent, like cyclodextrin, but still solubilizes amiodarone to give a clear aqueous solution of amiodarone which have better stability profile and is stable upon storage at room temperature for prolonged periods of time such as for at least 12 months, preferably 18 months or 2 years. Surprisingly, in spite of absence of surfactants, the dosage form of the present invention is stable in plastic/polymeric containers and no sorption of amiodarone takes place upon storage in plastic/polymeric containers over a period of time.

In one preferred embodiment, the pharmaceutically acceptable salt of amiodarone is the hydrochloride salt, although other suitable salts may also be used. Amiodarone or its pharmaceutically acceptable salt is present at a concentration that permits direct intravenous administration. Preferably, it is present at a concentration ranging from about 0.005 mg/ml to about 10.0 mg/ml; preferably, from about 1.0 mg/ml to about 7.0 mg/ml.

The ready-to-administer parenteral dosage form of the present invention may be selected from a pre-filled syringe or a 'ready-to-infuse' infusion dosage form. Suitably, the aqueous solution of amiodarone or its pharmaceutically acceptable salt is filled in a plastic container which may be a barrel of a pre-filled syringe or an infusion bag. The plastic container as used herein is a suitable container made up of a plastic or polymeric material. Non-limiting examples of plastic or polymeric material which may constitute the material of construction of the container include cyclic olefin polymers (COP), cyclic olefin copolymers (COC), polyolefin polymers like polyethylene, polypropylene; polycarbonates, modified polyolefin-polyethylene polymers or styrene-polyolefin based polymers and block co-polymers thereof. In preferred embodiments, the container is made up of a plastic or polymeric material selected from the group consisting of cyclo olefin polymers, cyclo olefin copolymers; polyolefin polymers; polycarbonates; styrene-polyolefin based polymers and block co-polymers thereof. Cycloolefin homopolymers (cycloolefin polymers, or COP) are homo polymers comprising single type of cycloolefin monomers. Cycloolefins (cyclic olefins) are mono or polyunsaturated, mono or polycyclic ring systems such as cycloalkenes (like cyclopropene, cyclopentene, cyclobutene), bicycloalkenes (like norbornene), tricycloalkenes, tetracycloalkenes and the like. The ring system can be monosubstituted or polysubstituted. Cycloolefin copolymers (COC) are made up from cycloolefins and co-monomers, wherein cycloolefins are copolymerized with small proportions of comonomers. Suitable co-monomers are unsubstituted or substituted olefins having 2 to 6 carbon atoms like ethylene, propylene and butylene. Preferably, according to one embodiment, the container has non-glass components. Suitably, the material of construction is such that these containers are transparent which makes it possible to carry out visual inspection of the drug solution prior to and during administration of the drug solution. Any change in colour or any particulate matter can be detected easily by visual inspection, which ensures safety. In one embodiment, the flexible plastic infusion container, which is the primary packaging container may be optionally further packaged in a secondary packaging. In one embodiment, the secondary packaging is designed to protect the solution from light. The secondary packaging may comprise a second container such as a pouch or overwrap or bag or carton. In preferred embodiments, the secondary packaging pouch or overwrap or carton is made up of a suitable light protective material such as aluminum. It may further comprise an oxygen scavenger placed between the plastic container and secondary packaging pouch.

In one embodiment, the ready-to-administer parenteral dosage form is a prefilled syringe and the plastic container is a cartridge or barrel fitted in the pre-filled syringe. In this specific embodiment, amiodarone or its pharmaceutically acceptable salt is present in a concentration ranging from about from about 1.0 mg/ml to about 8.0 mg/ml, preferably from about 2 mg/ml to 7 mg/ml, more preferably from about 3.0 mg/ml to about 6.0 mg/ml. In one specific embodiment, the amiodarone or its pharmaceutically acceptable salt is present at a concentration of 3 mg/ml. In another specific embodiment, the amiodarone or its pharmaceutically acceptable salt is present at a concentration of 6 mg/ml. Further, according to this embodiment wherein the parenteral dosage form is a prefilled syringe, the aqueous solution of amiodarone or its pharmaceutically acceptable salt is present in a volume ranging from about 10 ml to 100 ml, preferably 25 ml to 50 ml, more preferably 50 ml in one specific embodiment. In a preferred particular embodiment, amiodarone or its pharmaceutically acceptable salt is present at 6 mg/ml in a cartridge of pre-filled syringe having a volume of 50 ml. In another preferred particular embodiment, amiodarone or its pharmaceutically acceptable salt is present at 3 mg/ml in a cartridge of pre-filled syringe having a volume of 50 ml.

The cartridge or barrel of the pre-filled syringe is made up of appropriate plastic or polymeric material. In a preferred aspect, the syringe comprises a cartridge or barrel made up of cyclic olefin polymer (COP), cyclic olefin copolymer (COC), polyolefins such as polypropylene, polycarbonates and the like. In one preferred embodiment the cartridge or barrel of the prefilled syringe is made up of a polycyclo-olefin resin polymer. This type of material have a nitrogen transmission rate ranging from about 50-100 ml/(m$^2$.24 hour.atm); oxygen transmission rate ranging from about 250-320 ml/(m$^2$.24 hour.atm); carbon dioxide transmission rate ranging from about 800-1000 ml/(m$^2$.24 hour.atm). Such containers are available commercially and are manufactured by BD Medical Pharmaceutical Systems. The prefilled syringe may further comprise an elastomeric tip cap, made up of a suitable material such as chloro-butyl rubber formulation. The syringe may comprise a plunger stopper made up of rubber material such as bromo-butyl rubber or any other suitable material. The barrel, the elastomeric tip cap and the plunger stopper remains in contact with the aqueous solution of amiodarone throughout the storage shelf-life. The syringe may be further optionally packed in a secondary packaging to protect the solution from light. The secondary packaging may comprise a suitable pouch, such as an aluminum pouch and a carton packaging. The pouch may further contain an oxygen scavenger.

According to another embodiment of the present invention, the ready-to-administer parenteral dosage form is an infusion dosage form and the plastic container is a flexible infusion container such as an infusion bag or a flexible pouch or a soft bag wherein the aqueous solution of amiodarone is directly administered intravenously. In this specific embodiment, amiodarone or its pharmaceutically acceptable salt is present in the plastic container in a concentration ranging from about 0.5 mg/ml to about 2 mg/ml, preferably from about 1.0 mg/ml to 2 mg/ml, preferably 1.5 mg/ml in one specific embodiment and 1.8 mg/ml in another specific embodiment. Further, according to this embodiment, wherein the parenteral dosage form is an infusion dosage form, the aqueous solution of amiodarone or its pharmaceutically acceptable salt is present in the plastic container in a volume ranging from about 80 ml to about 800 ml, preferably from about 100 ml to 500 ml, incorporating all intermediate volumes. In one specific embodiment, the volume of the aqueous solution is 100 ml. In another specific embodiment, the volume of the aqueous solution is 200 ml. In one particular embodiment, the volume of the aqueous solution is 400 ml. In a preferred particular embodiment, the infusion bag has aqueous solution of amiodarone or its pharmaceutically acceptable salt at a concentration of 1.5 mg/ml and in a volume of 100 ml. In another preferred particular embodiment, amiodarone or its pharmaceutically acceptable salt is present at a concentration of 1.8 mg/ml and in a volume of 200 ml.

The concentration of amiodarone or its pharmaceutically acceptable salt and the volume of the aqueous solution of amiodarone filled in the plastic container is such that the prescribed dose of amiodarone can be conveniently delivered via single infusion bag or pre-filled syringe.

The infusion bag or flexible pouch or soft bag is made up of appropriate plastic or polymeric material. In a preferred aspect, the flexible infusion plastic container is not impermeable in nature and possesses some permeation characteristics and the aqueous solution of amiodarone remains in contact with these materials of the container throughout the shelf life of the dosage form. The container may be single or multiple layered and made up of a suitable material such as plastic or any other polymeric material. Such materials may be selected from, but not limited to, cyclo olefin polymers, cyclo olefin copolymers, polyolefin polymers such as polyethylene, polypropylene; modified polyolefin-polyethylene polymers or styrene-polyolefin based polymers and block co-polymers thereof. These plastic materials of the container may further have one or more outer layers which may be made up of polyamide, modified polyolefin, polypropylene, styrene-polyolefin based polymers and block co-polymers thereof and the like. In preferred embodiments, the flexible infusion plastic container may be made up of a material comprising a polymer of cyclic olefin such as cycloolefin homopolymer or cycloolefin copolymer or mixture thereof. Specifically, in a particular embodiment, the container comprises an inner layer made up of a cycloolefin polymer, a middle layer made up of linear low density polyethylene polymer and an outer layer made up of low density polyethylene polymer. This type of containers have a water vapour transmission rate of 2 g (m$^2$.day) when measured at (40° C./90% relative humidity); oxygen transmission rate of 570 ml/(m$^2$.24 hour.atm) when measured at (23° C./0% relative humidity) and carbon dioxide transmission rate of 3400 ml/(m$^2$.24 hour.atm) when measured at 23° C./0% relative humidity. Such containers are available commercially and are manufactured by Hosokawa as Polyelite EHC film bag. In another specific embodiment, the flexible infusion containers are made up of an outer layer of polyamide 11, a middle tie of modified polyolefin and an inner layer of linear low density polyethylene. This type of containers have a water vapour transmission rate of 2 g (m$^2$.day) when measured at (40° C./90% relative humidity); oxygen transmission rate of 900 ml/(m$^2$.24 hour.atm) when measured at (23° C./0% relative humidity) and carbon dioxide transmission rate of 600 ml/(m$^2$.24 hour.atm) when measured at 23° C./0% relative humidity. Such containers are available commercially and are manufactured by Hosokawa as Polyelite AE-1. In another embodiment, the flexible infusion containers may be made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially and are manufactured by Technoflex These type of containers have a water vapour transmission rate of 0.62 g (m$^2$.day) when measured at 23° C./60% relative humidity; oxygen permeability of 1110 ml/(m$^2$.24 hour.atm) when measured at 23° C./40% relative humidity and carbon dioxide transmission rate of 5149 ml/(m$^2$.24 hour.atm). Alternatively, the flexible plastic container used is made up of multilayer polyolefin film (M312 and M312A) with a multilayered polyolefin tubing (M916 and M916A). Such containers are available under the brand names of Sippex.

In one embodiment, the flexible infusion plastic containers have a single outlet for withdrawal of the aqueous solution from the container. The single outlet is a single infusion port or connector, which in one embodiment may have three assembled parts including a central stopper made up of chlorobutyl rubber (latex free); an upper breakable part and a bottom part, both made up of polycarbonate. Such ports are available under the brand names of Minitulipe®. In one specific embodiment, the stopper is made up of Minitulipe M95A spike port with chlorobutyl (latex free) 6321 GS joint Sippex 323. In one embodiment, the infusion port allows for insertion of an infusion set, cannula/needle prior to administration such that it allows a tight connection with the infusion line and allows for single outward flow of the aqueous solution. In one embodiment, the container and the delivery port connecting to the infusion needle forms a system whereby during intravenous administration of the solution to the patient, the vacuum created by outgress of solution is accommodated by the elasticity or flexibility of the perfusion container instead of ingress of external non-sterile air, which advantageously maintains and ensures sterility of the solution until it reaches the patient.

In one embodiment, the flexible infusion plastic container includes a thermally resealable portion that is fusible in response to thermal energy, and a container body having a sealed empty chamber in fluid communication with the resealable portion for receiving therein the aqueous solution of the present invention. The method of filling the container includes penetrating the resealable portion with an injection member and introducing the aqueous solution of the present invention into the chamber, withdrawing the injection member while engaging the base of the body to substantially prevent axial movement of the body, and applying thermal energy to the resealable portion to thermally fuse the penetrated region thereof. Such systems are elaborated in U.S. Pat. No. 7,992,597, which is incorporated herein by reference.

In another embodiment, the flexible infusion plastic container may include a chamber for receiving aqueous solution of the present invention and a thermoplastic portion in fluid communication with the chamber. The thermoplastic portion defines a penetrable region that is penetrable by a filling member and is heat resealable to hermetically seal an aperture therein by applying laser radiation at a predetermined wavelength and power and in a predetermined time period. Such systems are elaborated in U.S. Pat. No. 7,490,639, which is incorporated herein by reference.

In yet another embodiment, the flexible infusion plastic container include a sealed chamber; a first penetrable septum in fluid communication with the chamber that is formed of an elastic material and is penetrable by a first injection member to fill the first chamber with the aqueous solution of the present invention therethrough; and a second penetrable septum movable between first and second positions. In the first position, at least a portion of the second septum is spaced away from the first septum to allow the injection member to penetrate the first septum and aseptically or sterile fill the chamber with the aqueous solution of the present invention therethrough. In the second position, the portion of the second septum overlies and seals a resulting injection aperture in the first septum after withdrawal of the first injection member therefrom, and is penetrable by a second injection member to penetrate the first and second septums and withdraw the filled aqueous solution of the present invention from the chamber and through the second injection member. Such systems are elaborated in United States patent application number 20130333796, which is incorporated herein by reference.

The aqueous solution of amiodarone or its pharmaceutically acceptable salt, according to the present invention comprises an acid. The acid may be a suitable organic acid or an inorganic acid. Preferably, the acid is selected from the group of organic acids. The acid may be selected from, but not limited to, acetic acid, citric acid, lactic acid, tartaric acid, ascorbic acid, formic acid, propionic acid, butyric acid, oxalic acid, carbonic acid, lactobionic acid, hydrochloric acid, phosphoric acid. The acid may be selected from, acetic acid, citric acid, tartaric acid, propionic acid, oxalic acid. In one preferred embodiment, the acid is acetic acid or glacial acetic acid. The amount of acetic acid present in the aqueous solution may vary from about 1 mg/ml to about 15 mg/ml, i.e 0.1% w/v to 1.5% w/v, preferably from about 5 mg/ml to about 12 mg/ml. In specific preferred embodiments, acetic acid may be present in an amount of 6 mg/ml or 7 mg/ml or 8 mg/ml or 9 mg/ml or 10 mg/ml.

The aqueous solution of amiodarone or its pharmaceutically acceptable salt, according to the present invention further comprises a polyol. A polyol is a compound which has more than one hydroxyl groups. The polyols that may be used in the present invention may be selected from the group consisting of monomeric polyols, sugars, sugar alcohols or polymeric polyols. Non-limiting examples of polyols that may be used include glycerol, dextrose, propylene glycol, ethylene glycol, glucose, sucrose, mannose, sorbitol, mannitol, erythritol, xylitol, maltitol, lactitol, arabitol, inositol, polyethylene glycol, polypropylene glycol and the like. Suitable pharmaceutically acceptable grades of these polyols may be used, such as for example various grades of polyethylene glycols (PEG) like PEG 200, PEG 300, PEG 400, PEG 600, PEG900 etc. may be used. In one preferred embodiment, the polyol is glycerine or glycerol. In a further embodiment, the glycerine or glycerol may be present in the aqueous solution at a concentration ranging from about 5 mg/ml to 37 mg/ml (i.e. 0.5% w/v to 3.7% w/v); preferably from about 10 mg/ml to about 20 mg/ml, more preferably from about 12 mg/ml to about 18 mg/ml. In specific preferred embodiments, glycerin may be present in an amount of 15 mg/ml. In another preferred embodiment, the polyol is dextrose and it may be present in the aqueous solution at a concentration ranging from about 20 mg/ml to 72 mg/ml, preferably from about 25 mg/ml to about 50 mg/ml. In one specific preferred embodiment, dextrose may be used in an amount of 27 mg/ml.

The aqueous solution of amiodarone or its pharmaceutically acceptable salt, according to the present invention have a pH in the range of about 2.0 to 4.0. When the pH of the aqueous solution of the present invention was adjusted in the range of about 2.0 to 4.0, preferably about 2.5 to about 3.5, and the solution was stored in non-glass plastic container such as pre-filled syringe made up of appropriate plastic or polymeric material, the solution exhibited satisfactory chemical and physical stability. In one specific embodiment, the pH of the solution was adjusted to about 2.75. The pH of the solution may be adjusted in the desired range by use of a suitable pH adjusting agents and or a buffering agent known in the pharmaceutical art or it may be auto-adjusted in the desired range by the ingredients present in the solution of the present invention. The aqueous solution of amiodarone or its pharmaceutically acceptable salt, according to the present invention has an osmolality in the range of about 250-400 mOsm/kg, preferably 270-375 mOsm/kg. The osmolality of the aqueous solution may be adjusted by addition of an osmotic agent or tonicity adjusting agent known in the pharmaceutical art or it may be auto-adjusted in the desired range by the ingredients present in the solution of the present invention.

Preferably, the ready-to-administer parenteral dosage form of the present invention is free of solubilizers such as complexing or chelating agents like cyclodextrins or surfactants such as for example polysorbate 80, tween 80 etc.

Surprisingly, the inventors of the present invention have developed a ready-to-administer parenteral dosage form of amiodarone, which does not make use of solubilizers like surfactants and complexing agent, like cyclodextrin, but still solubilizes amiodarone to give a clear aqueous solution of amiodarone which have better stability profile and is stable upon storage at room temperature for prolonged periods of time such as for at least 12 months, preferably 18 months or 2 years. Surprisingly, in spite of absence of surfactants, the dosage form of the present invention is stable in plastic/polymeric containers and no sorption of amiodarone takes place upon storage in plastic/polymeric containers over a period of time.

In a preferred embodiment, the aqueous solution of amiodarone according to the present invention has a dissolved oxygen level of less than 4 ppm, preferably less than 2 ppm, more preferably less than 1 ppm. This is achieved by purging the aqueous solution with an inert gas such as nitrogen or argon or helium.

In one particularly preferred embodiment, the acid is acetic acid and the polyol is glycerine. In another particularly preferred embodiment, the acid is acetic acid and the polyol is dextrose (anhydrous). In another preferred embodiment, the acid is citric acid and the polyol is polyethylene glycol.

According to one preferred embodiment of the present invention, there is provided a stable, sterile, ready to administer parenteral dosage form of amiodarone comprising an aqueous solution comprising:
  a. amiodarone or its pharmaceutically acceptable salt,
  b. an acid which is acetic acid, and
  c. a polyol which is selected from glycerine or dextrose,
    wherein the pH of the solution is in the range of about 2.0 to 4.0,
    wherein the solution is filled in a plastic container selected from a cartridge of a prefilled syringe or an infusion bag, and wherein the solution is free of solubilizers.

The ready-to-administer parenteral dosage form of the present invention remains stable throughout the shelf life. In one embodiment, the parenteral dosage form of the present invention when subjected to long term stability testing at room temperature (25±2° C. and 60%±5% relative humidity) and at refrigerated conditions (2-8° C.) as well as at accelerated stability testing condition (40° C./75% RH) was found to be physically and chemically stable for the shelf life of the product and meets all acceptable stability criteria's upon storage for prolonged periods such as for at least 12 months, preferably 18 months or 2 years. Suitably, in terms of physical stability, the solution remained clear, with no precipitation or crystallization of the drug upon storage. Suitably, in terms of chemical stability, the assay of the drug remained within the specified limit and the impurities/related compounds remained within the specified limit upon storage.

The ready-to-administer parenteral dosage form of the present invention may be prepared by a process involving following exemplary steps: Purging water for injection with nitrogen. Dissolving an acid such as acetic acid into water for injection kept at 55-70° C. with stirring. Dissolving a polyol such as glycerin to the above solution by stirring. Maintaining the temperature of the solution at about 55-70° C. Gradually adding amiodarone or its pharmaceutically acceptable salt to the above bulk solution, and dissolving it under stirring. Maintaining the temperature of the solution at 55-70° C. during stirring. Cooling the solution to 20-25° C. and checking the pH and physical appearance. Filtering the solution aseptically through membrane filter. Filling the filtered solution aseptically in suitable plastic container like the pre-filled syringes or infusion bags and optionally packaging it with a secondary packaging such as an aluminum overwrap along with an oxygen scavenger.

Hereinafter, the invention will be more specifically described by way of Examples. The examples are not intended to limit the scope of the invention and are merely used as illustrations.

EXAMPLE 1

According to one preferred embodiment of the present invention, this example elaborates a ready-to-administer parenteral dosage form in the form of a pre-filled syringe comprising aqueous solution of amiodarone hydrochloride:

TABLE 1

Aqueous solution of amiodarone hydrochloride

| Ingredients | Amount in mg/ml | Amount in 50 ml Pre-filled syringe (mg) |
|---|---|---|
| Amiodarone hydrochloride | 6.0 | 300 |
| Acetic acid | 9.0 | 450 |
| Glycerine | 15.0 | 750 |
| Water for Injection | q.s. to 1 ml | q.s. to 50 ml |

Preparation: Nitrogen purged water for injection at temperature between 55-70° C. was taken and acetic acid was gradually added and dissolved under stirring in water for injection. The temperature of the solution was maintained at 55-70° C. during stirring. To this solution, glycerine was gradually added and dissolved by stirring. The temperature of the solution was maintained at 55-70° C. To this bulk solution, the active agent amiodarone hydrochloride was added gradually and dissolved under stirring. The temperature of the solution was maintained at 55-70° C. during stirring. The solution was allowed to stabilize and clarity of the solution was ensured visually. The solution was then cooled to 20-25° C. and the pH was checked which was between 2.6 and 2.9. The solution was checked for physical appearance and it was found to be clear and colorless. The solution was then filtered aseptically through a set of two 0.2 micron PES membrane capsule filters and the filtered solution was simultaneously filled aseptically in 50 ml COP pre-filled syringes (PFS). The barrel was stoppered aseptically with plunger stoppers. The pre-filled syringes were labeled and packaged in an aluminum over pouch.

Stability Testing: The aqueous solution filled in the pre-filled syringes, was subjected to long term stability testing and accelerated stability testing. For long term stability, the aqueous solution filled in the prefilled syringes was kept at 25° C./60% relative humidity and at refrigerated conditions of 2-8° C. For the accelerated stability study, solution was kept at 40° C./75% relative humidity. The stability study results at various time point are presented in Table 2 below:

TABLE 2

Results of Stability Study

| Storage condition | | Assay of drug (%) | Related substances - known Impurity (%) | | | | | Highest unknown impurity (%) | Total impurities (%) | pH of the solution | Osmolality (mOsm/kg) |
|---|---|---|---|---|---|---|---|---|---|---|---|
| | | | D | F | B | C | G | | | | |
| Initial | | 98.65 | 0.073 | ND* | ND | ND | ND | 0.01 | 0.084 | 2.9 | 335 |
| 2-8° C. | 1 M | 97.85 | 0.078 | ND | 0.003 | ND | ND | 0.01 | 0.094 | 2.66 | 333 |
| | 3 M | 99.37 | 0.072 | ND | ND | ND | ND | 0.021 | 0.104 | 2.91 | 332 |
| | 6 M | 97.63 | 0.075 | ND | ND | ND | ND | ND | 0.075 | 2.94 | 332 |
| | 12 M | 99.84 | 0.077 | ND | 0.002 | ND | ND | 0.009 | 0.106 | 2.65 | 332 |
| 25° C./ | 1 M | 99.54 | 0.107 | ND | 0.005 | ND | ND | 0.009 | 0.133 | 2.63 | 332 |
| 60% | 3 M | 97.9 | 0.145 | 0.005 | 0.005 | ND | ND | 0.02 | 0.187 | 2.71 | 332 |
| RH | 6 M | 97.49 | 0.207 | 0.003 | 0.008 | ND | ND | 0.022 | 0.261 | 2.83 | 331 |
| | 12 M | 96.08 | 0.386 | 0.009 | 0.023 | ND | ND | 0.046 | 0.545 | 2.64 | 332 |
| 40° C./ | 1 M | 96.68 | 0.387 | 0.007 | 0.011 | 0.005 | ND | 0.035 | 0.469 | 2.62 | 332 |
| 75% | 2 M | 97.88 | 0.69 | ND | ND | ND | 0.009 | 0.043 | 0.827 | 2.76 | 330 |
| RH | 3 M | 95.75 | 0.963 | 0.049 | 0.04 | 0.018 | ND | 0.049 | 1.181 | 2.68 | 331 |

*ND—Not Detected;
RH—Relative Humidity

It was found that the solutions remained clear and colourless, without any signs of precipitation or crystallization upon storage. The assay of the drug remained within the specified limit and the impurities/related compounds remained below the specified limit upon storage. The results indicate that the total impurities remained below 2.5% and the highest unknown impurity remained below 0.2% upon storage at room temperature (25° C./60% relative humidity) and at refrigerated conditions (2-8° C.) for at least 12 months. Among the various known impurities, the pertinent impurity D ((2-butylbenzofuran-3-yl)(4-hydroxy-3,5-diiodophenyl) methanone), which is a metabolite of amiodarone, remained below the limit of 1.6% (Limit—NMT 1.6% is as per BP monograph of Amiodarone intravenous infusion). Other known impurities such as Impurity A, E, H, the 2-butyl benzofuran impurity and the methoxyphenyl impurity were not detected at any time point. Further, the other known impurities such as Impurity B, C, F and G were either not detected or if detected at any time point, they were below the specified limit of not more than 0.2%. Also, the pH and osmolality of the amiodarone solution did not change (significantly) and is maintained in the desired range, upon storage.

EXAMPLE 2

According to another preferred embodiment of the present invention, this example elaborates a ready-to-administer parenteral dosage form in the form of an infusion dosage form comprising an infusion bag filled with aqueous solution of amiodarone hydrochloride:

TABLE 3

Aqueous solution of amiodarone hydrochloride:

| Ingredients | Amount in mg/ml | Amount in 100 ml infusion bag (mg) |
|---|---|---|
| Amiodarone hydrochloride | 1.5 | 150 |
| Acetic acid (glacial) | 9.0 | 900 |
| Glycerine | 15.0 | 1500 |
| Water for Injection | q.s. to 1 ml | q.s. to 100 ml |

Procedure: The aqueous solution of amiodarone was prepared following steps similar to the ones described in Example 1. The filtered solution so obtained was filled aseptically in a 100 ml infusion bag made up of cyclo-olefin polymer and sealed. The bags were labeled and packaged in an aluminum over pouch along with an oxygen scavenger.

Stability Testing: The filled infusion bag, having the aqueous solution of amiodarone, was subjected to stability testing as above at controlled room temperature of 25° C./40% relative humidity; at refrigerated conditions of 2-8° C. and at accelerated stability testing conditions, of 40° C./25% relative humidity. It was observed that upon storage, the solution remained clear and colourless, without any signs of precipitation or crystallization and the assay of the drug remained within the specified limit and the impurities/related compounds remained below the specified limit upon storage. The total impurities remained below 2.5% and the highest unknown impurity remained below 0.2%. Among the various known impurities, the pertinent impurity D ((2-butylbenzofuran-3-yl)(4-hydroxy-3,5-diiodophenyl) methanone), which is a metabolite of amiodarone, remained below the limit of 1.6% (Limit—NMT 1.6% is as per BP monograph of Amiodarone intravenous infusion). Further, the other known impurities were either not detected or if detected, they were below the specified limit of not more than 0.2%. Also, the pH and osmolality of the amiodarone solution did not change (significantly) and is maintained in the desired range, upon storage.

The invention claimed is:

1. A stable, sterile, ready to administer parenteral dosage form of amiodarone comprising an aqueous solution comprising:
   a) amiodarone or its pharmaceutically acceptable salt,
   b) acetic acid, and
   c) a polyol,
   wherein the pH of the solution is autoadjusted in the range of about 2.0 to 4.0 with acetic acid and the solution is otherwise free of a buffering agent,
   wherein the solution is filled in a plastic container,
   wherein the solution is free of a surfactant and is free of a cyclodextrin.

2. The ready to administer parenteral dosage form as claimed in claim 1, wherein the dosage form is a ready-to-administer infusion and the plastic container is a flexible infusion bag.

3. The ready to administer parenteral dosage form as claimed in claim 1, wherein the amiodarone or its pharmaceutically acceptable salt is present in the aqueous solution at a concentration ranging from 0.5 mg/ml to 2.0 mg/ml.

4. The ready to administer parenteral dosage form as claimed in claim 1, wherein the volume of aqueous solution ranges from 100 ml to 500 ml.

5. The ready to administer parenteral dosage form as claimed in claim 1, wherein the acetic acid is present at a concentration ranging from 5 mg/ml to 12 mg/ml.

6. The ready to administer parenteral dosage form as claimed in claim 1, wherein the polyol is glycerol and it is present at a concentration ranging from about 5 mg/ml to 37 mg/ml.

7. The ready to administer parenteral dosage form as claimed in claim 1, wherein the polyol is dextrose and it is present at a concentration ranging from about 20 mg/ml to 72 mg/ml.

8. The ready to administer parenteral dosage form as claimed in claim 1, wherein the container is made up of a plastic or polymeric material selected from the group consisting of cyclo olefin polymers, cyclo olefin copolymers, polycarbonates, polyolefin polymers, styrene-polyolefin based polymers and block co-polymers thereof.

\* \* \* \* \*